(12) United States Patent
Asif et al.

(10) Patent No.: US 10,414,899 B2
(45) Date of Patent: Sep. 17, 2019

(54) MARKERS FOR AQUEOUS COMPOSITIONS

(71) Applicants: Rohm and Haas Company, Collegeville, PA (US); Dow Global Technologies LLC, Midland, MI (US)

(72) Inventors: Zahid Asif, Collegeville, PA (US); Zhenwen Fu, Norristown, PA (US); Eric C. Greyson, Blue Bell, PA (US); Peilin Yang, Midland, MI (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 22 days.

(21) Appl. No.: 15/788,848

(22) Filed: Oct. 20, 2017

(65) Prior Publication Data

US 2018/0148565 A1      May 31, 2018

Related U.S. Application Data

(60) Provisional application No. 62/427,865, filed on Nov. 30, 2016.

(51) Int. Cl.

| | |
|---|---|
| *C08K 5/06* | (2006.01) |
| *C09D 7/63* | (2018.01) |
| *C09D 5/00* | (2006.01) |
| *C09D 133/12* | (2006.01) |
| *G01N 30/72* | (2006.01) |
| *C09D 5/33* | (2006.01) |

(52) U.S. Cl.
CPC .................. *C08K 5/06* (2013.01); *C09D 5/00* (2013.01); *C09D 5/004* (2013.01); *C09D 7/63* (2018.01); *C09D 133/12* (2013.01); *G01N 30/7206* (2013.01)

(58) Field of Classification Search
CPC ... C08K 5/06; C09D 7/63; C09D 5/00; C09D 5/004; C09D 133/12; G01N 30/7206
USPC .......................................................... 524/369
See application file for complete search history.

(56) References Cited

U.S. PATENT DOCUMENTS

| | | |
|---|---|---|
| 5,897,811 A | 4/1999 | Lesko |
| 5,902,750 A | 5/1999 | Fuerholzer et al. |
| 5,958,780 A | 9/1999 | Asher et al. |
| 6,812,309 B2 | 11/2004 | Clark |
| 2010/0041581 A1 | 2/2010 | VanGrasstek et al. |
| 2013/0210991 A1 | 8/2013 | Fonnum et al. |

FOREIGN PATENT DOCUMENTS

| | | | |
|---|---|---|---|
| CN | 101561625 A | 10/2009 | |
| EP | 1650045 A2 | 4/2006 | |
| WO | 2012177987 A1 | 12/2012 | |
| WO | WO-2012177987 A1 * | 12/2012 | ............. C07C 43/20 |
| WO | 2014081556 A1 | 5/2014 | |
| WO | 2014179646 A1 | 11/2014 | |

* cited by examiner

*Primary Examiner* — Ronald Grinsted
(74) *Attorney, Agent, or Firm* — Karl E. Stauss; Cantor Colburn LLP

(57) ABSTRACT

The present invention provides aqueous polymer compositions containing one or more, or, preferably, two or more triphenylmethyl alkyl aryl ether markers having a formula $(Ph_3C)_m Ar(OR)_n$, wherein Ph is a phenyl group, Ar is an aromatic ring containing group having from six to twenty carbon atoms, R is a $C_1$-$C_{18}$ alkyl group, m is an integer of from 1 to 2, and n is an integer of from 1 to 4. The markers are readily detectable, such as by mass spectroscopy, upon solvent extraction and separation from the aqueous polymer compositions, or from dried or cured coatings, film or layers thereof.

10 Claims, No Drawings

MARKERS FOR AQUEOUS COMPOSITIONS

The present invention relates to triphenylmethyl alkyl aryl ether compounds useful in a method for marking aqueous compositions, such as for use in coating compositions or traffic paint.

Waterborne quick drying traffic paint is a popular and low cost method of improving roadway safety. Government agencies responsible for roadways frequently specify use of selected polymer grades at minimum levels in paints sold to them. However, the same agencies struggle to confirm whether formulators have actually provided the specified polymer grade in the required amounts. Complete analytical take-apart is lengthy and expensive and is, thus, not practical. Some existing marker systems for such paints are quick and simple, but use detection techniques such as color or fluorescence, that do not work in all tints or which may suffer from interference from other raw materials or naturally occurring products in the paints. Some known detection methods require a developing solution, which add complexity. Several detection methods are not quantitative or sensitive to small amounts of marked materials; these can detect only a higher level presence but not quantity. Several markers carry unwanted side effects such as toxicity and/or require a high dosage level. Other markers do not have a broad range of temperature or pH stability and can be removed from the marked compositions in process or in use. Hydrophilic markers, for example, could be leached or washed from dry compositions or dried films limiting their use in identifying dry samples, such as coatings or paints that have been applied and cured. There remains a need for marker compounds for aqueous polymer compositions which are difficult to remove by drying the compositions, as a result of weather or as a result of repeated washing or wetting of the end use product, such as a coating or traffic marking.

World Intellectual Property Organization publication no. WO 2012177987A1, to Dow Chemical, discloses the use of triphenylmethyl alkyl aryl ether molecules as fuel markers which are detectable in fuels, including being detectable to some extent after combination of or adulteration of the fuels with impurities.

The present inventors have endeavored to find markers useful for marking aqueous polymer compositions, such as coatings, without altering the appearance or performance of the compositions while being detectable in the wet composition and dried or coatings made therefrom.

STATEMENT OF INVENTION

In accordance with the present invention, aqueous compositions, such as compositions useful for making coatings, or, preferably, traffic markings, comprise (i) one or more aqueous polymers, such as vinyl or acrylic emulsion polymers or polyurethane dispersions and (ii) 2 ppm to 100 ppm or, preferably, from 5 ppm to 50 ppm of one or more, or, preferably, at least two triphenylmethyl alkyl aryl ether compounds having a formula $(Ph_3C)_m Ar(OR)_n$, wherein Ph is a phenyl group, wherein Ar is an aromatic ring containing group having from six to twenty carbon atoms, or, preferably, from six to twelve carbon atoms, such as a phenyl or methylphenyl group, R is a $C_1$-$C_{18}$ alkyl group or, preferably, a $C_1$-$C_{12}$ alkyl group, or, more preferably, a $C_1$-$C_8$ alkyl group, m is an integer of from 1 to 2, and n is an integer of from 1 to 4, or, preferably, from 1 to 2.

In accordance with the present invention, the aqueous compositions comprising the (i) one or more aqueous polymers, such as vinyl or acrylic emulsion polymers or polyurethane dispersions have any of: (ii) two triphenylmethyl alkyl aryl ether compounds in a defined ratio, which can be any ratio of 0.01:1 to 1:01, or, preferably, from 0.1:1 to 1:0.1, or (ii) three triphenylmethyl alkyl aryl ether compounds in a defined or set ratio, which can be any ratio such that the marker having the highest concentration is present in no more than 100 times the concentration of the marker having the lowest concentration, for example, from 0.01:0.01:1.0 to 1.0:0.01:1.0.

In accordance with the present invention, the aqueous compositions comprising the (i) one or more aqueous polymers, such as vinyl or acrylic emulsion polymers, polyurethane dispersions or aqueous solution polymers, such as polyamines, polymeric polyacids or alkali soluble polymers, and (ii) the one or more triphenylmethyl alkyl aryl ether compounds have a pH of from 3 to 12 or, preferably, from 7 to 11.

In accordance with the present invention, in the aqueous compositions comprising the (i) one or more aqueous polymers, and (ii) the one or more triphenylmethyl alkyl aryl ether compounds, the (i) one or more aqueous polymer is preferably a vinyl or acrylic emulsion polymer, such as an acrylic emulsion polymer, or, more preferably, an acrylic emulsion polymer comprising butyl acrylate in polymerized form.

In accordance with the present invention, in the aqueous compositions comprising the (i) one or more aqueous polymers, and (ii) the one or more triphenylmethyl alkyl aryl ether compounds, the (i) one or more aqueous polymer is a vinyl or acrylic emulsion polymer which is an anionically stabilized emulsion polymer and, wherein the composition further comprises one or more polyamine and one or more volatile base, such as ammonia, an alkyl amine, such as ethyl amine amine alcohols, or, preferably, ammonia.

In accordance with the present invention, aqueous compositions comprise (ii) the one or more triphenylmethyl alkyl aryl ether compounds, one or more anionically stabilized emulsion polymer as the (i) one or more aqueous polymers, and one or more polyamine and one or more volatile base, the amount of the one or more polyamine ranges from 0.1 to 2 wt. % or, preferably, from 0.25 to 1.5 wt. % solids based on total polymer solids.

In accordance with the present invention, the aqueous compositions comprising the (i) one or more aqueous polymers, and (ii) the one or more triphenylmethyl alkyl aryl ether compounds further comprise one or more pigments, extenders, and/or fillers. The one or more pigments, extenders and/or fillers preferably comprise, a pigment, such as a white or opacifier pigment, preferably, titanium dioxide, combined with one or more fillers and/or extenders, preferably calcium carbonate, calcium oxide, silica, silicates, and combinations thereof. As used herein, the term "filler" and the term "extender" are used interchangeably.

In accordance with the present invention, the aqueous compositions comprising the (i) one or more aqueous polymers, and (ii) the one or more triphenylmethyl alkyl aryl ether compounds further comprise one or more high boiling coalescent chosen from diacid esters, phosphate esters, isobutyrate esters, alkyl esters of fatty acids, fatty ethers, fatty glycerides, fatty acid amides, alkoxylates of fatty acids, addition (co)polymer coalescents, ethylene and propylene glycol ethers having a normal boiling point of 150 to 300° C., and mixtures thereof, preferably, isobutyrate esters. The amount of the coalescent may range from 4.0 wt. % to 30 wt. %, based on total polymer solids or, preferably, from 5 to 20 wt. %.

In another aspect of the present invention, methods of detecting a marker of (ii) one or more or, preferably, two or more, triphenylmethyl alkyl aryl ether compounds having a formula $(Ph_3C)_m Ar(OR)_n$, wherein Ph is a phenyl group, wherein Ar is an aromatic ring containing group having from six to twenty carbon atoms, or, preferably, from six to twelve carbon atoms, such as a phenyl or methylphenyl group, R is a $C_1$-$C_{18}$ alkyl group or, preferably, a $C_1$-$C_{12}$ alkyl group, or, more preferably, a $C_1$-$C_8$ alkyl group, m is an integer of from 1 to 2, and n is an integer of from 1 to 4, or, preferably, from 1 to 2 in a composition of (i) one or more aqueous polymers, such as vinyl or acrylic emulsion polymers, polyurethane dispersions, aqueous solution polymers, such as polyamines, polymeric polyacids or alkali soluble polymers, or a dried or cured film, coating or layer formed therefrom, which methods comprise: extracting the one or more triphenylmethyl alkyl aryl ether compounds from the aqueous composition or the dried or cured film, coating or layer formed therefrom, using a solvent, such as xylene or toluene, to form a marker extract, separating from the marker extract the (ii) one or more triphenylmethyl alkyl aryl ether compounds by chromatographic separation, such as by gas chromatography (GC) or liquid chromatography (LC), and detecting the (ii) one or more or, preferably, two or more $C_1$-$C_{12}$ alkyl phenyl ethers in the marker extract, such as by mass spectroscopy (MS).

In the methods of the present invention, the extraction of the dried or cured film, coating or layer formed from the aqueous composition when the dried or cured film, coating or layer was formed on a substrate comprises separating or removing the film coating or layer on a substrate from the substrate, such as by scraping the film, coating or layer or with a wire brush, followed by grinding or milling the resulting solids, and then extracting to form the marker extract and detecting the marker.

In the methods of the present invention, the extraction of the dried or cured film, or layer formed from the aqueous composition when the dried or cured film, or layer is freestanding comprises grinding or milling the dried or cured film coating or layer solids, and then extracting to form the marker extract and detecting the marker.

Unless otherwise indicated, conditions of temperature and pressure are room temperature and standard pressure, also referred to herein as "ambient conditions".

In the instant specification, percentages are weight percentages (wt. %) and temperatures are in ° C., unless specified otherwise. All boiling points mentioned herein are measured at atmospheric pressure (760 mm/Hg). Concentrations are expressed either in parts per million ("ppm") or parts per billion ("ppb") calculated on a weight/weight basis, or on a weight/volume basis (mg/L); preferably on a weight/volume basis.

The singular forms "a," "an," and "the" include plural referents unless the context clearly dictates otherwise.

All phrases comprising parentheses denote either or both of the included parenthetical matter and its absence. For example, the phrase "(meth)acrylate" includes, in the alternative, acrylate and methacrylate.

As used herein, the term "acid monomer or anionic monomer" means ethylenically unsaturated carboxylic acid monomer in either the acid or anionic form ($COO^-$).

As used herein, the term "alkali soluble polymer" means an aqueous polymer which is soluble at a pH of from 8 to 14 such as acrylic and vinyl polymers having from 10 to 50 wt. %, based on the total weight of monomers used to make the polymer, of an ethylenically unsaturated carboxylic acid or its salt.

As used herein, the term "alkyl" group is a substituted or unsubstituted saturated hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are unsubstituted. Preferably, alkyl groups are linear or branched.

As used herein, the term "alkenyl" group is an alkyl group having at least one carbon-carbon double bond. Preferably, alkenyl groups have one or two carbon-carbon double bonds, preferably one.

As used herein, the term "aqueous" means water or water mixed with up to 16 wt. %, or up to 6 wt. %, or, preferably, up to 0.5 wt. % of a water miscible solvent which is volatile under ambient conditions, such as a lower alkanol.

As used herein, the term "capillary column" is a column suitable for gas chromatography having an inner diameter from 75 to 750 µm, preferably, from 100 to 550 µm, such as from 150 to 350 µm and a length of 5 to 100 m, preferably 7 to 60 m.

As used herein, unless otherwise indicated, the term "emulsion polymer" refers to a polymer made by aqueous emulsion polymerization.

As used herein, the term "ethylenically unsaturated carboxylic acid monomer" refers to acrylic acid, methacrylic acid, beta-acryloxypropionic acid, ethacrylic acid, α-chloroacrylic acid, α-vinylacrylic acid, crotonic acid, α-phenylacrylic acid, cinnamic acid, chlorocinnamic acid, β-styrylacrylic acid, maleic acid, itaconic acid, citraconic acid, and salts thereof.

As used herein, the term "(meth)acrylate" means acrylate, methacrylate, and mixtures thereof and the term "(meth) acrylic" used herein means acrylic, methacrylic, and mixtures thereof.

As used herein, the term "phenyl" group is a substituent derived from phenol or another aromatic hydrocarbon compound. A phenyl group has a total of six ring atoms, unless otherwise specified, and has one ring.

As used herein, the term "polymeric polyacid" refers to polymers and copolymers of ethylenically unsaturated carboxylic acid monomers or salts thereof, the copolymers comprising, in polymerized form, at least 80 wt. % or, preferably, at least 90 wt. % of the ethylenically unsaturated carboxylic acid monomer or salt, based on the total weight of monomers used to make the polymer.

As used herein, the term "total polymer solids" or "polymer solids" means the total solids of the one or more vinyl or acrylic emulsion polymers and the polyurethanes or polyurethane prepolymers in the aqueous compositions.

As used herein, the term "road" includes any indoor or outdoor solid surface that is or may be constantly or intermittently traveled on by pedestrians, moving vehicles, tractors, or aircraft. Some non-limiting examples of a "road" include highways, streets, driveways, sidewalks, runways, taxiing areas, tarmac areas, and parking lots.

As used herein, the phrase "wt. %" stands for weight percent.

The present invention provides a way for users, makers and sellers of aqueous polymer compositions, for example, traffic paint, and coatings, to quickly and with a high level of sensitivity detect the source and identity of polymer compositions they buy, resell, use or find. The users, makers and sellers can verify the source and identity of aqueous polymer compositions regardless of when or how they obtain them. For government agencies and others, the present invention enables quality verification. For other makers, users and sellers, the present invention provides a way to determine what aqueous polymer compositions third parties and customers are using. Detection can be performed using, for example, GC/MS. The compositions that can be effectively tested include both aqueous and dry or cured compositions, such as already applied paints or coatings or already formed films, layers or moldings. The low concentration of the compounds as markers (down to 2 ppm) enables discrete marking of the aqueous polymer compositions without introducing odor or otherwise impacting the performance or appearance of final products, such as coatings, made with those compositions.

The present invention provides a method for marking an aqueous polymer composition, the method comprising adding (ii) the one or more or, preferably, two or more triphenylmethyl alkyl aryl ether compounds having a formula $(Ph_3C)_m Ar(OR)_n$, wherein Ph is a phenyl group, wherein Ar is an aromatic ring containing group having from six to twenty carbon atoms, or, preferably, from six to twelve carbon atoms, such as a phenyl or methylphenyl group, R is a $C_1$-$C_{18}$ alkyl group or, preferably, a $C_1$-$C_{12}$ alkyl group, or, more preferably, a $C_1$-$C_8$ alkyl group, m is an integer of from 1 to 2, and n is an integer of from 1 to 4, or, preferably, from 1 to 2 to an aqueous polymer composition. Suitable aqueous polymer compositions can be, for example binders, coating additives, polymer dispersions (i.e. HYPOD etc.), and other aqueous emulsion or dispersion polymers.

The (ii) triphenylmethyl alkyl aryl ether compounds of the present invention can simply be added to an aqueous polymer composition while it is being formed, such as in polymerization, or afterword, as in formulation.

The aqueous compositions comprising the (i) one or more aqueous polymers, and (ii) the one or more triphenylmethyl alkyl aryl ether compounds may optionally comprise conventional additives, such as surfactants, wetting agents, plasticizers, defoamers, rheology modifiers, antioxidants, colorants, matting agents, pigments or colorants.

The one or more (ii) triphenylmethyl alkyl aryl ether compounds may be placed in the aqueous polymer composition directly, or alternatively, placed in an additives package containing other materials, e.g. pigments, fillers or colorants, dispersants, surfactants, defoamers, rheology modifiers, etc., and the additives package is added to the aqueous polymer composition.

In the aqueous polymer compositions of the present invention for use in making traffic markings, suitable concentrations of fillers, extenders and/or pigments may range from 50 to 90 wt. % or, preferably, from 60 to 85 wt. %, of total solids of polymer, coalescent, filler, extender and pigment.

The aqueous polymer compositions of the present invention may not comprise fillers, extenders and/or pigments and may be a polymeric binder, such as an emulsion polymer or polyurethane dispersion, for use in clearcoats and custom formulations.

Suitable vinyl or acrylic polymers for use in the present invention may be prepared from a wide range of suitable addition polymerizable ethylenically unsaturated monomers, such as, for example, nonionic ethylenically unsaturated monomers, including arylenes, such as styrene, vinyl toluene, and α-methyl styrene; butadiene; olefins; vinyl esters; vinyl halides; vinylidene chloride; (meth)acrylonitrile; $C_1$-$C_{40}$ alkyl esters of (meth)acrylic acid; for example, methyl (meth)acrylate, ethyl (meth)acrylate, n-butyl (meth)acrylate, 2-ethylhexyl (meth)acrylate, and other (meth)acrylates.

The vinyl or acrylic polymers of the present invention may be formed by conventional emulsion polymerization of addition polymerizable monomers, such as in the presence of a thermal or redox initiator and one or more surfactants.

The anionically stabilized emulsion polymers of the present invention are emulsion polymers which comprise one or more anionic surfactants or which comprise, in copolymerized form, an ethylenically unsaturated carboxylic acid monomer or salt thereof, for example, acrylic acid, or both.

To limit water sensitivity the anionically stabilized emulsion polymers of the present invention comprise 18 wt. % or less, or, preferably, 4 wt. % or less, or, preferably, 2 wt. % or less of the ethylenically unsaturated carboxylic acid monomer or salt in copolymerized form, based on the total weight of all monomers.

To limit water sensitivity the anionically stabilized emulsion polymers of the present invention may comprise 4 wt. % or less or, preferably, 2 wt. % or less of the one or more anionic surfactants.

Preferably, the triphenylmethyl alkyl aryl ether compounds (ii) are represented by formula (I)

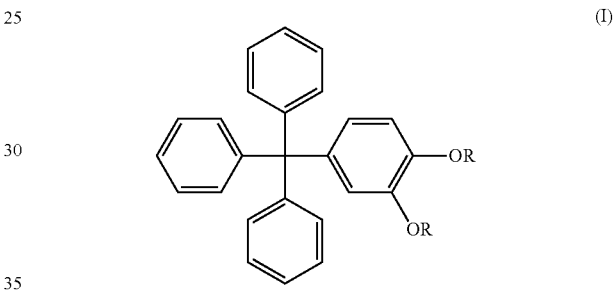

(I)

wherein R is $C_1$-$C_{18}$ alkyl, preferably $C_2$-$C_{18}$ alkyl, preferably $C_2$-$C_{16}$ alkyl, preferably $C_2$-$C_{12}$ alkyl, preferably $C_3$-$C_{12}$ alkyl, preferably $C_3$-$C_{10}$ alkyl. An example of a preferred marker is 3-(sec-butyl)-4-(decyloxy)phenyl)methanetril)tribenzene. Preferably, the compounds of the present invention are represented by formula (II)

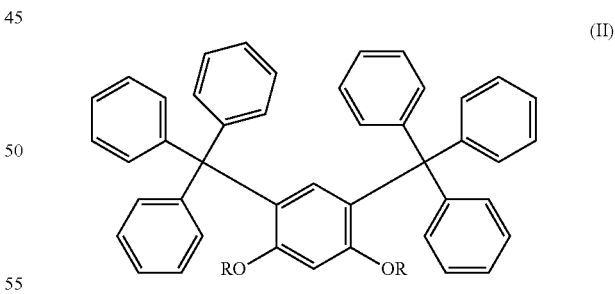

(II)

wherein R is $C_1$-$C_{18}$ alkyl, preferably $C_2$-$C_{18}$ alkyl, preferably $C_2$-$C_{16}$ alkyl, preferably $C_2$-$C_{12}$ alkyl, preferably $C_3$-$C_{12}$ alkyl, preferably $C_3$-$C_{10}$ alkyl.

The triphenylmethyl alkyl aryl ether compounds (ii) of this invention may be prepared by methods known in the art, such as, for example, alkylation of phenols or polyhydroxyaromatics with trityl halide or alcohol, followed by alkylation with organic halides in the presence of base. For example, tritylated phenolic ethers may be prepared according to the following reaction scheme, wherein M is one or two and N is 1 to 4.

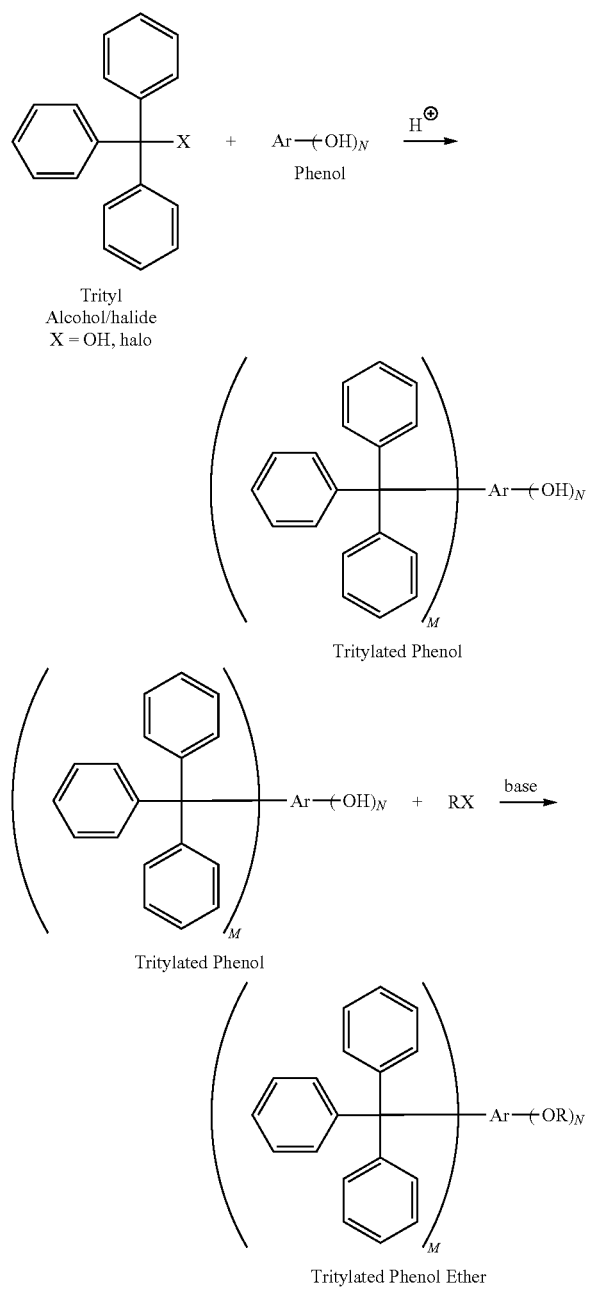

The (ii) the one or more triphenylmethyl alkyl aryl ether compound markers of the present invention are UV and heat stable, and provide little or no volatility in ambient use conditions, and at temperatures of up to 80° C. at atmospheric pressure.

In using (ii) the one or more triphenylmethyl alkyl aryl ether compounds of the present invention as markers, preferably the minimum amount of each compound added to an aqueous polymer composition to be marked is at least 2 ppm, or, preferably at least 5 ppm, or, preferably, at least 10 ppm. Preferably, the maximum amount of each marker is 50 ppm, or, preferably 30 ppm or less, or, more preferably 25 ppm or less. Preferably, the maximum total amount of marker compounds is 100 ppm, or, preferably, 50 ppm, or, more preferably, 30 ppm.

Preferably, the (ii) the one or more triphenylmethyl alkyl aryl ether compounds of the present invention are not detectable by visual means in the marked aqueous polymer composition, i.e., it is not possible to determine by unaided visual observation of color or other characteristics that it contains a marker compound. Preferably, a marker compound is one that does not occur normally in the aqueous polymer composition to which it is added, either as a constituent of the polymer itself, or as an additive used therein.

Preferably, more than one marker compound is present. Use of multiple marker compounds facilitates incorporation into the aqueous polymer composition of coded information that may be used to identify the origin and other characteristics of the aqueous polymer composition. The code comprises the identities and relative amounts, e.g., fixed integer ratios, of the marker compounds. One, two, three or more marker compounds may be used to form the code. Marker compounds according to the present invention may be combined with other markers.

In accordance with the compositions of the present invention, two or more of (ii) the triphenylmethyl alkyl aryl ether compound markers could be used at various predetermined ratios. Combinations of markers can be used as digital marking systems, with the ratios of amounts forming a code for the marked product. Additional compounds useful as markers would be desirable to maximize the available codes. Thus, the present invention could be used broadly to provide end-users or regulators verification that a given aqueous polymer composition was used in a given project.

Preferably, the marker compounds are detected by at least partially separating them from constituents of the aqueous polymer composition using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) spectral analysis, such as UV spectrophotometry. Identities of the marker compounds preferably are determined by mass spectral analysis.

Preferably, the compounds are at least partially separated from the marked liquid using two-dimensional gas chromatography, preferably with different columns in the two GC separations. Preferably, mass spectral analysis is used to detect the marker compounds in the aqueous polymer composition without performing any separation. Alternatively, marker compounds may be concentrated prior to analysis, e.g., by drying the aqueous polymer composition.

Further, and more preferably, a gas chromatographic method for detecting a marker compound in an aqueous polymer composition comprises: (a) extracting the marker from an aqueous polymer composition by solvent extraction with an organic solvent, preferably, xylene, (b) injecting a sample of the extract into a first capillary column which is an open tubular column, preferably, coated with a polysiloxane stationary phase, and allowing the sample to flow through the first capillary column to produce a first effluent stream; (b) allowing the first effluent stream to pass through a detector and identifying a retention time range in the first effluent stream which includes a retention time of the marker compound; (c) introducing only a portion of the first effluent stream which is within the retention time range into a second capillary column which is an open tubular column coated with either (i) an ionic sorbent or (ii) a polyethylene glycol, and allowing said portion to flow through the second capillary column to produce a second effluent stream; and (d) allowing the second effluent stream to pass through a detector.

Suitable detectors can be any one capable of detecting the marker; preferably a flame ionization detector (FID), atomic emission detector, pulsed discharge helium ionization detector, dielectric barrier detector, thermal conductivity detector, helium ionization detector, mass selective detector (e.g., a mass spectrometer (MS)); preferably a FID or MS.

Preferably, when a mass spectrometer is used as a detector the column diameter is no greater than 400 μm, preferably no greater than 350 μm, or, preferably no greater than 330 μm. Preferably, capillary columns are made from polyimide-coated fused silica glass or passivated metal.

Preferably, the amount of aqueous polymer composition sample injected into the gas chromatograph is from 0.2 to 5 μl, preferably from 0.5 to 3 μl, preferably from 0.8 to 2 μl. Preferably the injection is split such that the ratio of total injection to the amount sent to the first column is from 25:1 to 15:1, preferably about 20:1. Preferably, the oven temperature for the first column initially is from 25 to 200° C., preferably from 50 to 150° C., preferably from 40 to 100° C. and then increases to a temperature from 300 to 450° C., preferably from 325 to 425° C., preferably from 350 to 400° C. Preferably, the oven temperature for the second column follows the same profile as that for the first column. Preferably, the carrier gas (preferably helium) flow rate is from 0.2 to 5 mL/min, preferably from 0.5 to 4 mL/min, preferably from 0.5 to 2 mL/min. Those skilled in the art will appreciate that the parameters mentioned above are interrelated and are not critical individually, but they can be adjusted together to achieve optimum separation of the desired compounds.

Preferably, the ionic sorbent is an inorganic salt or a mixture of inorganic salts; preferably sodium or potassium or barium salts or a mixture thereof; preferably sodium sulfate, potassium sulfate, barium sulfate, chlorides of sodium, potassium or barium, or a mixture thereof. Especially preferred ionic sorbents include sodium sulfate, potassium sulfate, barium chloride, barium sulfate or a mixture thereof, preferably barium sulfate or potassium sulfate.

Preferably, the polyethylene glycol has a number average molecular weight from 10,000 to 30,000, preferably from 15,000 to 25,000. An especially preferred polyethylene glycol is CARBOWAX 20M. Preferably, when a mass spectrometer is used as a detector, the second column is a polyethylene glycol column.

EXAMPLES

Preparation of an Aqueous Polymer Composition in a Marked Formulation:

A triphenylmethyl alkyl aryl ether compound (3-(sec-butyl)-4-(decyloxy)phenyl)methanetriyl)tribenzene) was dissolved in a diisobutyrate ester plasticizer (Texanol™ plasticizer, Eastman Chemc., Kingsport, Tenn.) at a 375 ppm concentration. The 375 ppm solution was added to an acrylic emulsion polymer binder (anionically stabilized BA/MMA emulsion copolymer, 50.5 wt. % solids) to yield a marker concentration of 3.75 ppm, based on the total aqueous composition.

Extraction Conditions:

The formulation was extracted using xylene. 1 mL of marked formulation was mixed with 10 mL of xylene in a 20-mL vial. The solution was shaken for 30 min. 1.5 mL the present invention was then transferred to a centrifuge vial and centrifuged at 35000 rpm for 20 min. The supernatant was transferred to an autosampler vial for GC/MS analysis.

GC/MS Conditions:

A two-dimension GC system with mass selective detector was used in examples, as described in Table 1, below.

TABLE 1

| GC/MS Conditions | |
| --- | --- |
| Instrument: | Agilent 7890 GC with 5975 Mass Selective Detector (MSD) with Extractor Electron Impact ionization source |
| Column: | DB-35MS, 15-m × 0.25-mm ID, 0.25-μm film |
| Injector: | Injection volume: 3 μL Solvent wash: 6 times pre-injection and 6 times post-injection with acetone Sample washes: 3 times Sample pump: 3 times |
| Inlet: | Liner: Agilent Ultra-inert Splitless liner or equivalent Temperature: 280° C. Splitless injection Carrier gas: helium |
| Oven Temperature Programming: | 100° C. (0 min), 20° C./min to 280° C. (10 min), then 20° C./min to 340° C. (5 min). Total run time: 27 min |
| MSD Parameters: | Transfer line temperature: 340° C. EI source temperature: 350° C. Quad temperature: 200° C. EM offset: 106 V SIM ion: m/z 532 (100 ms dwell time) and 455 (100 ms dwell time). Plot m/z 532 only. |

1. Agilent Technologies, Santa Clara, CA.

With xylene extraction, the inventive triphenylmethyl alkyl aryl ether compounds marker was detected at 12% of the dosed concentration. Accordingly, the marker can be consistently detected at different concentration levels with a limit of detection of 2 ppm.

We claim:

1. An aqueous composition comprising (i) one or more aqueous polymers, and (ii) from 2 to 100 ppm of one or more compounds selected from a ethers having a formula (Ph3C)mAr(OR)n, wherein Ph is a phenyl group, Ar is an aromatic ring containing group having from six to twenty carbon atoms, R is a C1-C18 alkyl group, m is an integer of from 1 to 2, and n is an integer of from 1 to 4.

2. The composition as claimed in claim 1, wherein the (i) one or more aqueous polymers is chosen from vinyl or acrylic emulsion polymers, polyurethane dispersions and aqueous solution polymers.

3. The composition as claimed in claim 1, wherein the amount of the (ii) one or more compounds selected from ethers having a formula (Ph3C)mAr(OR)n ranges from 5 to 50 ppm.

4. The composition as claimed in claim 1, wherein the composition comprises (ii) two compounds selected from ethers having the formula (Ph3C)mAr(OR)n in a defined ratio to one another.

5. The composition as claimed in claim 1, wherein at least one of the (ii) one or more compounds selected from ethers having a formula (Ph3C)mAr(OR)n, wherein R is a C1-C12 alkyl group and Ar is an aromatic ring of six to twelve carbon atoms.

6. The composition as claimed in claim 1, wherein at least one of the (ii) one or more compounds selected from ethers having a formula (Ph3C)mAr(OR)n, wherein n is an integer of from 1 to 2.

7. The composition as claimed in claim 1, having a pH of from 3 to 12.

8. The composition as claimed in claim 1, further comprising one or more pigments, extenders and/or fillers.

9. The composition as claimed in claim 1, wherein the (i) one or more aqueous polymer is a vinyl or acrylic emulsion polymer which is an anionically stabilized emulsion polymer and, wherein the composition further comprises one or more polyamine and one or more volatile base.

10. A method of detecting a marker of (ii) one or more ether compounds having a formula (Ph3C)mAr(OR)n, wherein Ph is a phenyl group, Ar is an aromatic ring containing group having from six to twenty carbon atoms, R is a C1-C18 alkyl group, m is an integer of from 1 to 2, and n is an integer of from 1 to 4 in an aqueous composition of (i) one or more aqueous polymers, or a dried or cured film, coating or layer formed therefrom, the method comprising:

extracting the one or more ether compounds from the aqueous composition or the dried or cured film, coating or layer formed therefrom using a solvent to form a marker extract;

separating from the marker extract the (ii) one or more ether compounds by chromatographic separation; and, detecting the (ii) one or more ether compounds in the marker extract.

* * * * *